(12) United States Patent
D'Urso et al.

(10) Patent No.: US 7,697,808 B2
(45) Date of Patent: Apr. 13, 2010

(54) MULTI-TIPPED OPTICAL COMPONENT

(75) Inventors: Brian R. D'Urso, Clinton, TN (US); John T. Simpson, Clinton, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 11/873,139

(22) Filed: Oct. 16, 2007

(65) Prior Publication Data

US 2008/0080816 A1    Apr. 3, 2008

Related U.S. Application Data

(63) Continuation-in-part of application No. 11/421,547, filed on Jun. 1, 2006, which is a continuation-in-part of application No. 10/900,248, filed on Jul. 27, 2004, now Pat. No. 7,150,904, and a continuation-in-part of application No. 10/900,249, filed on Jul. 27, 2004, now Pat. No. 7,258,731.

(51) Int. Cl.
*G02B 6/04* (2006.01)
(52) U.S. Cl. ..................................... 385/115; 359/361
(58) Field of Classification Search ............... 385/1, 385/11, 40, 123, 131–132; 436/805
See application file for complete search history.

(56) References Cited

U.S. PATENT DOCUMENTS

| | | | |
|---|---|---|---|
| 3,284,332 A | 11/1966 | Gladrow et al. | |
| 3,586,895 A | 6/1971 | Sowers et al. | |
| 5,141,312 A | * 8/1992 | Thompson et al. | .......... 356/218 |
| 5,192,278 A | * 3/1993 | Hayes et al. | .................. 606/15 |
| 5,234,594 A | 8/1993 | Tonucci | |

(Continued)

FOREIGN PATENT DOCUMENTS

WO    WO 99/64909    12/1999

(Continued)

OTHER PUBLICATIONS

Tong et al. "Optical silica nanowires for nanophotonics," 2005, ICO20: Materials and nanotechnologies, Proc. Of SPIE, V. 6029, pp. 60290A-1-60290A-6.*

(Continued)

*Primary Examiner*—Frank G Font
*Assistant Examiner*—Peter Radkowski
(74) *Attorney, Agent, or Firm*—Novak Druce + Quigg; Gregory A. Nelson; Gregory Lefkowitz

(57) ABSTRACT

An optical component has a plurality of parallel noncontiguous optical conduits of at least one protrusive phase material embedded in a recessive phase material that acts as a support structure. The optical conduits extend from a proximal surface to a distal surface of the optical component. The distal surface has a plurality of spaced apart surface features of the protrusive phase material. Each independent optical conduits act as waveguides for a wavelength or range of wavelengths. The optical component can be formed such that the protruding surface features at the distal end of the component form an ordered array. An optical instrument can include the optical component in conjunction with a light source for illuminating a sample and a detector in optical communication optical component via the optical conduits.

16 Claims, 4 Drawing Sheets

U.S. PATENT DOCUMENTS

| | | | |
|---|---|---|---|
| 5,244,636 A * | 9/1993 | Walt et al. | 422/82.07 |
| 5,332,681 A * | 7/1994 | Tonucci et al. | 438/493 |
| 5,493,169 A | 2/1996 | Pierle | |
| 5,633,972 A * | 5/1997 | Walt et al. | 385/116 |
| 5,664,036 A * | 9/1997 | Islam | 385/31 |
| 5,690,894 A * | 11/1997 | Pinkel et al. | 506/23 |
| 5,814,524 A * | 9/1998 | Walt et al. | 436/518 |
| 5,837,196 A * | 11/1998 | Pinkel et al. | 422/55 |
| 5,859,937 A * | 1/1999 | Nomura | 385/12 |
| 5,952,665 A * | 9/1999 | Bhargava | 250/483.1 |
| 6,014,251 A * | 1/2000 | Rosenberg et al. | 359/350 |
| 6,016,376 A * | 1/2000 | Ghaemi et al. | 385/116 |
| 6,023,540 A * | 2/2000 | Walt et al. | 385/12 |
| 6,052,238 A * | 4/2000 | Ebbesen et al. | 359/738 |
| 6,104,945 A * | 8/2000 | Modell et al. | 600/473 |
| 6,146,593 A * | 11/2000 | Pinkel et al. | 422/68.1 |
| 6,200,737 B1 * | 3/2001 | Walt et al. | 430/320 |
| 6,231,744 B1 * | 5/2001 | Ying et al. | 205/324 |
| 6,266,459 B1 * | 7/2001 | Walt et al. | 385/12 |
| 6,327,410 B1 * | 12/2001 | Walt et al. | 385/115 |
| 6,406,845 B1 * | 6/2002 | Walt et al. | 435/6 |
| 6,417,506 B1 * | 7/2002 | Pinkel et al. | 250/216 |
| 6,482,593 B2 * | 11/2002 | Walt et al. | 435/6 |
| 6,483,640 B1 * | 11/2002 | Tonucci et al. | 359/361 |
| 6,660,363 B1 | 12/2003 | Barthlott | |
| 6,795,617 B2 * | 9/2004 | Dinu et al. | 385/42 |
| 6,800,860 B2 * | 10/2004 | Dietz et al. | 250/458.1 |
| 6,813,402 B2 * | 11/2004 | Narita et al. | 385/12 |
| 6,846,635 B1 * | 1/2005 | Anderson et al. | 435/7.1 |
| 6,853,786 B2 * | 2/2005 | Russell et al. | 385/125 |
| 6,859,570 B2 * | 2/2005 | Walt et al. | 385/12 |
| 6,890,764 B2 * | 5/2005 | Chee et al. | 436/518 |
| 6,893,816 B1 * | 5/2005 | Beattie | 435/6 |
| 6,926,927 B2 * | 8/2005 | Ishida | 427/250 |
| 6,931,177 B2 * | 8/2005 | Suzuki et al. | 385/33 |
| 6,934,443 B2 * | 8/2005 | Hikichi et al. | 385/31 |
| 6,951,715 B2 * | 10/2005 | Cunningham et al. | 435/4 |
| 6,960,528 B2 * | 11/2005 | Chen et al. | 438/695 |
| 6,970,247 B2 * | 11/2005 | Yankielun | 356/436 |
| 6,979,830 B2 * | 12/2005 | Dietz et al. | 250/485.1 |
| 6,991,939 B2 * | 1/2006 | Walt et al. | 436/172 |
| 7,006,741 B1 * | 2/2006 | Yu | 385/121 |
| 7,031,566 B2 * | 4/2006 | Kochergin et al. | 385/27 |
| 7,057,832 B2 * | 6/2006 | Wu et al. | 359/811 |
| 7,060,431 B2 * | 6/2006 | Chee et al. | 435/6 |
| 7,167,615 B1 * | 1/2007 | Wawro et al. | 385/37 |
| 7,167,622 B2 * | 1/2007 | Temelkuran et al. | 385/123 |
| 7,258,731 B2 * | 8/2007 | D'Urso et al. | 106/2 |
| 7,348,181 B2 * | 3/2008 | Walt et al. | 436/172 |
| 7,384,797 B1 * | 6/2008 | Blair | 436/524 |
| 7,394,547 B2 * | 7/2008 | Tan et al. | 356/480 |
| 7,400,399 B2 * | 7/2008 | Wawro et al. | 356/328 |
| 7,405,034 B2 * | 7/2008 | Yan et al. | 430/312 |
| 7,421,173 B2 * | 9/2008 | Mazur et al. | 385/123 |
| 2001/0029049 A1 * | 10/2001 | Walt et al. | 436/518 |
| 2002/0009719 A1 * | 1/2002 | Walt et al. | 435/6 |
| 2002/0142150 A1 | 10/2002 | Baumann et al. | |
| 2002/0149584 A1 | 10/2002 | Simpson et al. | |
| 2002/0150726 A1 | 10/2002 | Nun et al. | |
| 2002/0150909 A1 * | 10/2002 | Stuelpnagel et al. | 435/6 |
| 2002/0151245 A1 | 10/2002 | Hofmann et al. | |
| 2002/0154882 A1 * | 10/2002 | Moran | 385/137 |
| 2002/0171029 A1 * | 11/2002 | Wolff | 250/201.3 |
| 2002/0176646 A1 * | 11/2002 | Wu et al. | 385/12 |
| 2003/0013795 A1 | 1/2003 | Nun et al. | |
| 2003/0032204 A1 * | 2/2003 | Walt et al. | 436/518 |
| 2003/0044855 A1 * | 3/2003 | Anderson et al. | 435/7.9 |
| 2003/0077058 A1 * | 4/2003 | Russell et al. | 385/125 |
| 2003/0094035 A1 * | 5/2003 | Mitchell | 73/105 |
| 2003/0174992 A1 * | 9/2003 | Levene et al. | 385/129 |
| 2003/0207326 A1 * | 11/2003 | Su et al. | 435/7.1 |
| 2003/0230118 A1 * | 12/2003 | Dawes et al. | 65/379 |
| 2004/0004779 A1 * | 1/2004 | Kochergin et al. | 359/885 |
| 2004/0028875 A1 * | 2/2004 | Van Rijn et al. | 428/98 |
| 2004/0045932 A1 * | 3/2004 | Kochergin et al. | 216/59 |
| 2004/0093906 A1 * | 5/2004 | Gerstner et al. | 65/409 |
| 2004/0242023 A1 * | 12/2004 | Yan et al. | 438/780 |
| 2004/0254457 A1 * | 12/2004 | van der Weide | 600/430 |
| 2005/0013536 A1 * | 1/2005 | Walt | 385/27 |
| 2005/0072192 A1 * | 4/2005 | Arimondi et al. | 65/393 |
| 2005/0174425 A1 * | 8/2005 | Harris | 348/45 |
| 2005/0191774 A1 * | 9/2005 | Li et al. | 438/22 |
| 2005/0207713 A1 * | 9/2005 | Mazur et al. | 385/123 |
| 2005/0221279 A1 * | 10/2005 | Carter et al. | 435/4 |
| 2006/0024478 A1 | 2/2006 | D'Urso et al. | |
| 2006/0209301 A1 * | 9/2006 | Gardner et al. | 356/301 |
| 2007/0123776 A1 * | 5/2007 | Aharoni et al. | 600/437 |
| 2007/0138376 A1 | 6/2007 | Naughton | |
| 2007/0154154 A1 * | 7/2007 | Falkenstein et al. | 385/125 |
| 2007/0281130 A1 | 12/2007 | D'Urso et al. | |

FOREIGN PATENT DOCUMENTS

| | | |
|---|---|---|
| WO | WO 02/098562 | 12/2002 |
| WO | WO 03/013827 | 2/2003 |
| WO | WO 2005/118501 | 12/2005 |
| WO | WO 2006/091235 | 8/2006 |

OTHER PUBLICATIONS

Chang et al. "Nanofiber optic sensor based on the excitation of surface plasmon wave near fiber tip," 2006, Journal of Biomedical Optics, V. 11, N. 1, pp. 014032-1-014032-5.*

Tong et al., "Subwavelength-diameter silica wires for microscale optical components," 2005, Optical Components and Materials II, Proc. of SPIE V.5723, pp. 105-112.*

Liu et al, "Fabrication of Anodic-Alumina Films with Custom-Designed Arrays of Nanochannels," 2005, Adv. Mater., V. 17, N. 2, pp. 222-5.*

Tong et al. "Submicron and nano-diameter silica wires for optical wave guiding," 2002, Nano-Optics and Nano-Structures, Proc. Of SPIE V. 4923, pp. 52-58.*

Tong et al., "Modeling of subwavelength-diameter optical wire waveguides for optical sensing applications," 2005, Advanced Sensor Systems and Applications II, Proceedings of SPIE, V. 5634, pp. 416-423.*

Mazur, E., "Silica nanowires manipulating light at the nanoscale," LASE 2006 Conference Abstract 6107-21, Session 5, p. 97.*

McAuley et al., Silicon Micromaching Using a High-Density Plasma Source, Inst. of Physics Publishing, 2001, vol. 34, pp. 2769-2774.

Litvinova, Tunable Superhydrophobic Surfaces Fabricated by Nanosphere Lithography, MRS Bulletin, 2004, pp. 229-230.

Kim et al., Nanostructured Surfaces for Dramatic Reduction of Flow Resistance in Droplet-Based Microfluidics, IEEE, 2002, pp. 479-482.

Krupenkin et al., From Rolling Ball to Complete Wetting: The Dynamic Tuning of Liquids on Nanostructured Surfaces, Langmuir, 2004, vol. 20, pp. 3824-3827.

Tonucci et al., Nanochannel Array Glass, Science, 1992, vol. 258, pp. 783-785.

Erbil et al., Transformation of a Simple Plastic into a Superhydrophobic Surface, Science, 2003, vol. 299, pp. 1377-1380.

* cited by examiner

MULTI-TIPPED OPTICAL COMPONENT

CROSS-REFERENCE TO RELATED APPLICATIONS

The present application is a continuation-in-part (CIP) of U.S. patent application Ser. No. 11/421,547 filed on Jun. 1, 2006 by D'Urso and Simpson entitled "Optical Composite, Ordered Material Having Sharp Surface Features" which was a continuation-in-part (CIP) of U.S. application Ser. No. 10/900,248 filed on Jul. 27, 2004 by D'Urso and Simpson entitled "Composite, Ordered Material Having Sharp Surface Features", now U.S. Pat. No. 7,150,904 and U.S. patent application Ser. No. 10/900,249 filed on Jul. 27, 2004 by D'Urso and Simpson entitled "Composite, Nanostructured, Super-Hydrophobic Material", now U.S. Pat. No. 7,258,731 the entirety of the three is herein incorporated by reference.

STATEMENT REGARDING FEDERALLY SPONSORED RESEARCH

The United States Government has rights in this invention pursuant to contract No. DE-AC05-00OR22725 between the United States Department of Energy and UT-Battelle, LLC.

BACKGROUND OF THE INVENTION

Tapering an optical waveguide (also known in many instances as an optical fiber) below its transmission cutoff diameter causes the propagating light to form an evanescent field at the waveguide tip. If nothing couples to this evanescent field, the propagating light undergoes total internal reflection (TIR) and returns to the light source. If any evanescent field coupling occurs the amount of reflected light is proportionally reduced. Near-field scanning optical microscopy (NSOM) uses this phenomenon to achieve spatial resolution performance beyond the classical diffraction limit by employing a sub-wavelength light source or detector positioned in close proximity to a specimen.

Individual optical waveguides have been drawn down to approximately 100 nm and addressed optically as microscopy or sensor probes. In certain applications, it is desirable to scan a large area. In other applications it is desirable to probe many regions over an area simultaneously. Unfortunately, scanning a large area using a single probe is time consuming because of the small size of the probes. In addition, individual probes cannot simultaneously probe many regions over a given area. What is needed is a microscope or sensor probe design which provides a large number of sharp tips oriented in parallel that is operable for scanning a large area quickly, permitting simultaneous probing of many regions over a given area.

BRIEF SUMMARY OF THE INVENTION

The invention is an optical component where a recessive phase material forms a support structure within which is embedded a plurality of noncontiguous optical conduits of at least one protrusive phase material, where the conduits extend from a proximal surface to a distal surface of the optical component. The distal surface has a plurality of spaced apart surface features of the protrusive phase material protruding from the support structure where each surface feature reduces in cross sectional area as it extends from the support structure with the lowest cross sectional area found at the distal ends of the plurality of features. Each independent optical conduits act as waveguides for a wavelength or range of wavelengths where light reflects into the optical conduit when it encounters the interface between the protrusive and recessive material. Different optical conduits in the array of conduits can direct the same or different wavelengths or range of wavelengths through the conduits. The reflection can result when the recessive phase has a lower index of refraction than that of the protrusive phase or by the presence of a reflective material, such as a metallic material, situated at the interface between the protrusive phase and the recessive phase. The optical component can be formed such that the protruding surface features at the distal end of the component are arranged in an ordered array.

The invention is also directed to an optical instrument where the optical component described above is used in conjunction with a light source for illuminating a sample, so that light interacts with the sample, enters the optical component through the protrusive features at the distal end of the optical component, and is received by a detector in optical communication with the proximal end of the optical component, where the detector converts the light signal propagated through the optical component into an electrical signal. The instrument can also include a power supply, a controller, a processor, a display, and a frame to support the optical component.

Figure 1:
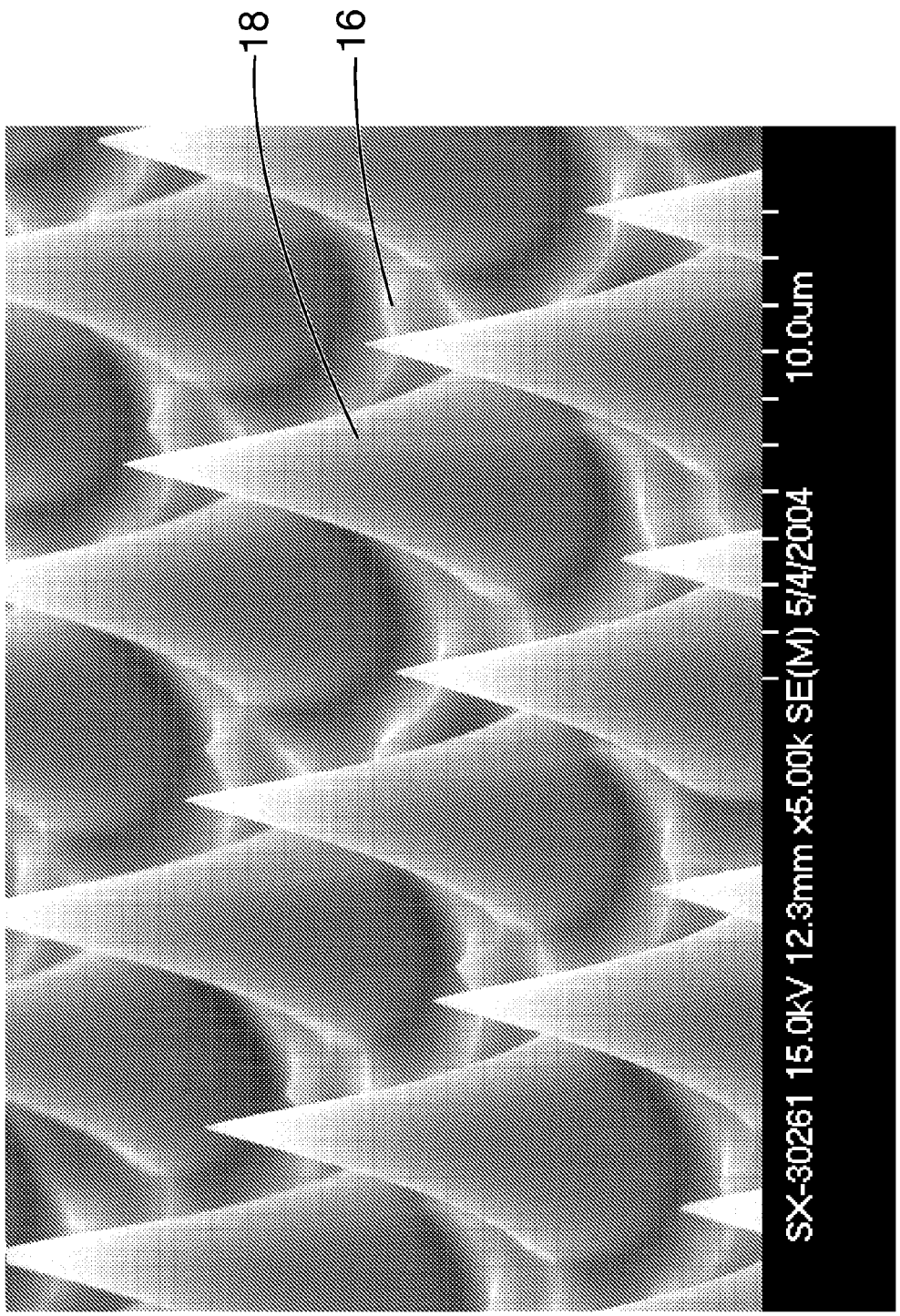
FIG. 1 is an oblique photomicrograph of a spiked glass plate after etching in accordance with an embodiment of the present invention.

For a better understanding of the present invention, together with other and further objects, advantages and capabilities thereof, reference is made to the following disclosure and appended claims in connection with the above-described drawings.

DETAILED DESCRIPTION OF THE INVENTION

The invention provides an optical component characterized by an individually addressable ordered array of optical waveguides (probes). Thus, a large area or a plurality of locations can be probed simultaneously with exceptional spatial resolution by using the array of optical waveguides.

Related U.S. Pat. No. 7,150,904 to D'Urso et al. entitled "Composite, Ordered Material Having Sharp Surface Features" (hereafter '904) discloses a process to form differentially etched, ordered materials having sharp surface features. '904 is based upon a composite structure including a recessive phase material and a protrusive phase material. The respective phases provide differential etchability, the recessive phase having a greater etchability than the protrusive phase. By subjecting the surface of the composite structure to an etchant that removes more of the recessive phase than the protrusive phase, the portion of the protrusive phase exposed to the etchant forms sharp, protruding surface features. The phrase "sharp surface feature" is defined therein to mean a generally tapered, protrusive structure that preferably terminates in a sharp terminus, ideally an atomically sharp point or ridge. "Sharp surface feature" can therefore refer to a feature having a base portion having a first cross sectional area, and a tip portion opposite the base portion having a reduced cross sectional area that is no more than 30% of the first cross sectional area, such as 25%, 20%, 15%, 10%, 8%, 6%, 5%, 4%, 3%, 2%, 1%, or less than 1% of the first cross sectional area. The reduction in cross sectional area in traversing from the base portion to the tip portion is preferably monotonic.

Sharp surface features disclosed in '904 include, for example, protrusions such as spikes and/or ridges. The protrusive phase is sharpened because the protrusive phase etches in the process, but at a slower rate than the recessive phase and because the distal tip is exposed for a greater period of time than the base portion as the recessive phase must be removed before significant surface area of the protrusive phase can be etched. The use of any differentially etchable recessive and protrusive materials in any combination to produce the desired effect is considered to fall within the scope of the present invention. Moreover, there are no limits to the variations of sizes and shapes of the sharp surface features. The composite base material may be made from any materials differentially etchable by any known etching method or methods.

The composite base material disclosed in '904 may be made from any materials which have suitable differential etching characteristics. Suitable materials include, for example, glasses, metals (including alloys), ceramics, polymers, resins, and the like. Choices of materials can have an effect on properties of the product, such as, for example, chemical resistance, ease and/or need of coating, strength, toughness, flexibility, elasticity, and plasticity.

The etchant disclosed in '904 can comprise: an organic or inorganic acid or alkali; polar, nonpolar, organic, inorganic, or mixed solvent; or mixtures of any of the foregoing. The etchant is selected to etch the composite material differentially as described herein. For example, an aqueous acid such as HF, HCl, HBr, or HI might be selected to etch glass compositions differentially.

The etchant disclosed in '904 can be a "mixed etchant system" which is comprised of a plurality of etchants that give different etch contrast ratios when applied to the composite surface. For example, one etchant can preferentially etch one phase while the other etchant can preferentially etch the other phase. A mixed etchant system can be particularly useful because the contrast ratio of the etching process can be modified by changing the composition and/or relative concentrations of the etchants. An example of a mixed etchant system is a mixture of HF and HCl. The possible compositions of suitable mixed etchant systems are virtually without limits.

The method by which the etching is carried out is not critical to the disclosed in '904 invention, as long as the desired surface feature is achieved. For example, other, non-solution etching techniques may be used, such as plasma etching or other isotropic etch techniques. The spiked composite material disclosed in '904 can be manufactured in a manner analogous to the process for making the well-known microchannel or nanochannel glass.

In one disclosed embodiment in '904, composite rods, having a core of a different material (the protrusive phase material) than the matrix material (the recessive phase material), are bundled in an aligned array, or bundle. The matrix material and core material are preferably selected based on differential etchability (susceptibility to etching or dissolution). In the case of the nano-channel glass, the core glass has a much higher etchability than that of the matrix glass. In the case of the previously unknown spiked surface disclosed in '904, the core material has a lower etchability than the matrix material, and forms protrusive, sharp features upon etching of the composite surface.

As disclosed in '904, the bundle can be heated to a temperature sufficient to soften the materials comprising the bundle, but below a temperature where damage, decomposition, or other deleterious changes can occur. The bundle is then drawn along the axis of the bundled rods to fuse and reduce the diameter of the bundle. The drawn bundle has reduced size material rod matrix material and respective core material. The drawn bundle is disclosed to be cut transversely into sections which can be re-bundled to increase the number of core material in the cross-section thereof. The bundle can then be drawn again. The twice-drawn bundle has further reduced size material rod matrix material and respective core material. The twice-drawn bundle can be cut transversely again into sections which can be re-bundled to increase the number of core material cores in the cross-section thereof.

As disclosed in '904, the process of bundling, drawing, and cutting can be performed a single time or repeated many times until the desired diameter, spacing, and number or conduits of the core material is obtained. Core material diameters and spacing on the nanometer scale are possible. The sizes of bundles and the number of rods contained therein can be varied throughout the process as desired.

As disclosed in '904, subsequently, one or both of the cut (composite) surfaces of the plate is etched to create an array of spikes of core protrusive material on one or both sides of the plate. The composite surface can be contacted with an etchant, (HF, for example), which etches the matrix material (recessive phase) faster than the core material (protrusive phase). The etching continues until the recessive matrix material is etched back to the desired depth, leaving some of the core material protruding from the surface. The result is that the etched core material is sharpened to a cone-shaped spike, the aspect ratio of the spike being dependent on the ratio of the matrix material and core material etching rates. FIG. 1 shows an embodiment of '904 having recessive areas of recessive phase 16 and spikes of protrusive phase 18. '904 does not disclose or suggest using the articles disclosed therein for optical applications. Moreover, the example glasses disclosed in '904 do not inherently form an optical waveguide without a reflective material inserted between the glasses because the disclosed core glasses for recessive phase 16 comprising Sylvania SG12™ or CORNING 0120™ are lower refractive index glasses than CORNING 8161™ disclosed therein for the protrusive phase 18.

Returning to the present invention, protrusive phase 18 is a solid material which is used as an optical waveguide also referred to as an optical conduit for the purposes of the present invention. The optical conduits are generally, but not necessarily cylindrical in shape between the proximal and distal ends of the optical component. Light of a selected wavelength or range or wavelengths (e.g. infrared, visible, and/or ultraviolet light) may be transmitted through an optical conduit of the protrusive phase dielectric material 18. The differentially etched, composite, ordered material having sharp surface features can thus be used as an array of optical waveguides having sharp pointed tips.

In one embodiment of the invention, for practical optical components, an optical conduit is realized by having the refractive index (nf) of the core material comprising the protrusive phase that exceeds the nf of the recessive phase, which functions as the cladding, by at least about 0.1 percent at a selected wavelength or wavelength range. The greater the difference of nf the more the light intensity is concentrated to the core region. Too small an index difference leads to the spatial energy spread significantly protruding into the cladding phase. For example, a core phase having an nf of 1.46 can have a cladding with an nf of 1.45, and generally act as a very good waveguide. An array can have a common recessive material but different protrusive materials for individual optical conduits such that individual optical conduits can have different optical properties.

Figure 2:
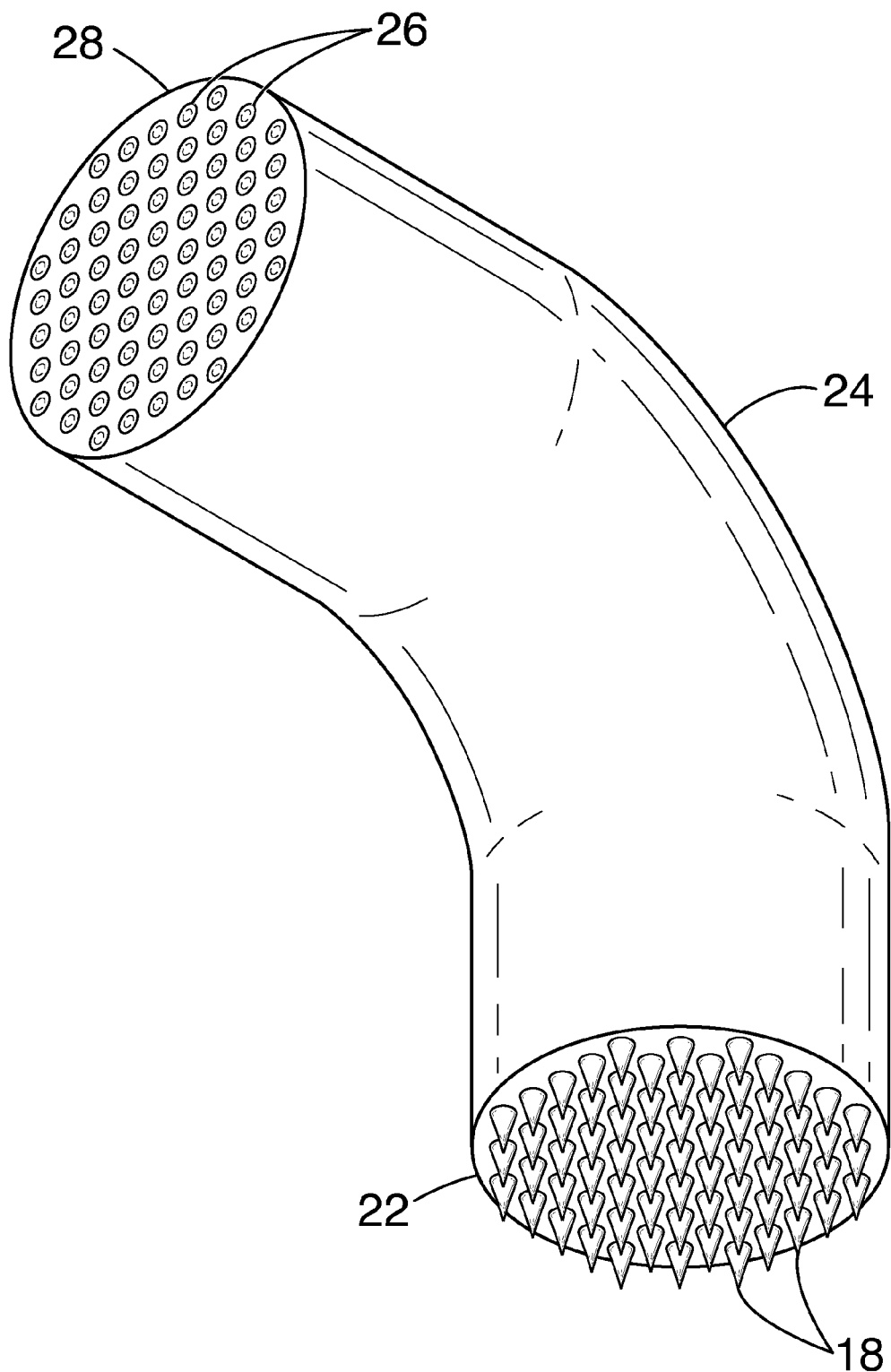
FIG. 2 is a not-to-scale schematic illustration of an optical component in accordance with an embodiment of the present invention.

FIG. 2 shows an optical component 24 having a distal end 22 that comprises an array of optical waveguides having sharp surface feature tips or spikes 18. Such an array can have from as few as two to more than one billion per square centimeter of individual, parallel, optical waveguides having sharp points that can be used as massively parallel sensors, parallel scanning optical microscopy probes, and the like. The optical waveguides comprising optical component 24 can be optical conduits of any desired length and diameter, a plate or wafer of any desired thickness and diameter, or any other desired size and shape. The optical waveguides comprising optical component 24 can be flexible or rigid, elastic or inelastic. The individual strands of protrusive phase that form the discrete tips or spikes 18 and their associated optical conduits run parallel to one another and completely (continuously) through the optical component 22 and are thus individually addressable as discrete areas 26 at a proximal end 28. In a typical arrangement, the optical waveguides are optical conduits comprising the protrusive phase having circular cross-sections surrounded by the ambient (e.g. air which provides the required surrounding other dielectric material with a lower refractive index) adjacent the tips or spikes 18. The protrusive phase is generally surrounded by the recessive phase in regions other than adjacent to the tips or spikes 18. To achieve individual addressability from discrete areas 26 at a proximal end 28, in a typical embodiment the recessive phase is a dielectric material having a lower refractive index compared to the protrusive phase material.

It can be understood from the description hereinabove that at least the protrusive phase must be sufficiently optically transparent at the selected wavelength(s) to be characterized as an optical waveguide. For the purposes of describing the present invention, an optical waveguide is defined as a material wherein the attenuation length of light of the selected wavelength(s) is at least as long as the average length of the sharp surface features of the protrusive phase. It is preferable that the attenuation length of light of selected wavelength(s) be at least ten times as long as the average length of the sharp surface features of the protrusive phase.

The selected wavelengths of light are guided (confined) through the protrusive phase. In one embodiment, the mechanism for guiding light through the optical conduit is for the protrusive phase to be characterized by a higher index of refraction than the recessive phase for at least one selected wavelength, a selected range of wavelengths, or a group of selected wavelengths of light. The protrusive phase thus acts as a waveguide for the selected wavelength(s) of light. In an alternate embodiment, the recessive phase can be reflective or a reflective interface material can be present between the recessive and protrusive materials, such that light at the selected wavelengths is reflected, thus confining the selected wavelengths of light to the protrusive phase. For example the recessive phase or an interface material can be a metal or metal alloy.

The reflection that occurs at the interface of the recessive and protrusive phase materials can be enhanced by the formation of a metallic "mirror" film at the interface. Various methods can be employed to generate this film. One method comprises drawing recessive glass tubes into which soft metal, such as gold, or metal composite, such as gold or gold-silver composite, coated protrusive glass rods have been placed. The soft (low melting point) metal will tend to melt as the glasses soften. As the glasses get drawn, the molten metal conforms to the interface between the narrowing tube and rod. The recessive glass tubes also coalesce into the support structure. As the glasses cool and harden so will the metal forming the mirror surface around the narrowed protrusive rod. Combined with bundling, fusing, wafer cutting, and etching, as described above, metal mirrored arrays can thus be formed.

A second method of forming a metal mirrored protruding phase involves using a high temperature melting metal (such as platinum and tungsten) coated glass rod to form the arrays. These metal coated glass rods can be inserted through the core of recessive glass tubes. The recessive glass tubes can then be drawn such that it coalesces around the metal coated rod without the metal melting or softening as the tube is drawn. Subsequent cutting, bundling, and fussing, as described above, can be used to create a metal mirrored array.

The metal can then be etched along with the recessive and protrusive glasses. Depending on the relative rates of etching, various recessed or protruding metal features can result. By proper choice of the etchant or mixture of etchants a desired structure can be formed at the distal end of the optical component. By use of a metal or other reflective material at the interface of the protrusive phase optical conduit and the recessive phase support structure, the protrusive phase can have a refractive index that is greater than, equal to, or less than the recessive phase yet perform the required waveguide function.

For some applications, it may be desirable to produce the optical conduits in the form of a long column with the protrusive surface features at the distal end of the column to transmit the selected wavelengths of light over a distance through the protrusive phase. Moreover, it may be desirable to produce tapered conduits with the sharp surface features protruding from the tapered distal end of the conduit while a larger cross section proximal end of the conduit is more easily and individually addressed. Such tapering conduits are particularly easy to produce if the material is produced by drawing and bundling glass fibers as disclosed in '904 and described above.

The present invention can be used in two basic modes. In a first mode of operation, light guided through the protrusive phase from the proximal end propagates to the sharp, protrusive features at the distal end, interacts with an analytical sample, and returns back through the protrusive phase to the proximal end as an optical data signal to a receiver or array of receivers contacted at the proximal end. In a second mode of operation, light directed onto an analytical sample via another means interacts with the sample, is picked up by the sharp protrusive features at the distal end, and is guided through the protrusive phase to a receiver or array of receivers connected to the proximal end.

It can thus be seen that the invention can be utilized in various optical instruments that operate in one or both of the above described modes. Potential applications of the present invention include analytical processes where small regions of space need to be optically probed, particularly in cases where it is desirable to probe many regions over an area simultaneously.

Figure 4:
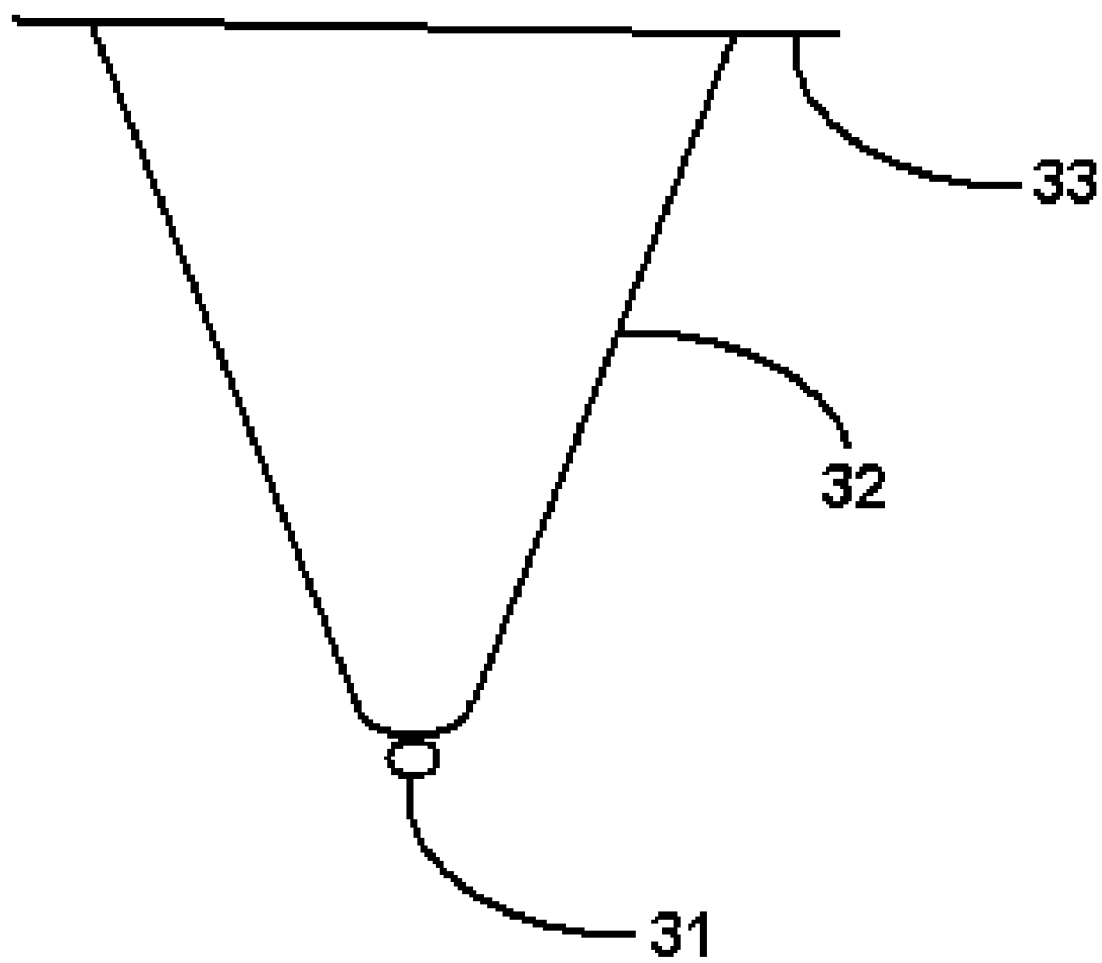
FIG. 4 shows an illustration of a metal nanoparticle attached to a single protrusive phase in accordance with an embodiment of the invention.

In one embodiment, the probe tips are functionalized to change their optical response as a result of biological or environmental contaminates or other chemical constituents. One functionalization embodiment of the invention leads to the formation of Surface Enhanced Raman Spectroscopy (SERS) probes. FIG. 4 shows a metal nanoparticle 31, such as a gold nanoparticle adhering to a single protruding feature 32 extending from the support structure 33 at a distal end of an optical component of one embodiment of the invention that can be employed for a SERS probe. Specifically, in the SERS embodiment, the distal (protrusive) end of the probes can be modified with SERS active structured nanoparticles, so that the multiple nanoparticle containing probe tips can be used for SERS as a multi-tipped sensor or probe, with the option of spatially resolving the signal. Using the evanescent optical fields of each protrusive feature, an array of protrusive features can be used instead of a single tip in a probe, thus gathering many data points in parallel and accelerating the image acquisition process. The protruding tips can be coated with a thin adhesive layer, for example a monolayer of ethyleneimine deposited from solution, and brought in contact with a surface decorated with nanoparticles of gold or some other metal, which adheres metal nanoparticles to the protrusive features.

As a fiber with sharp features on the end, the invention may be used as a biological probe. In particular, an intracellular probe connected to an optical microscope or spectroscope can be formed from the fiber with sharp features on an end.

In most configurations, instruments that use the optical component of the present invention may also include, but are not limited to: a light source for illuminating a sample so that light interacts with the sample and enters the optical component through the protrusive features at the distal end; a detector for converting a light signal propagated through the optical component into an electrical signal; various electrical components for supplying power to the instrument, controlling the instrument, processing the electrical signal into data, and displaying the data; and a support frame for supporting the optical component and generally at least some of the various components described herein.

Figure 3:
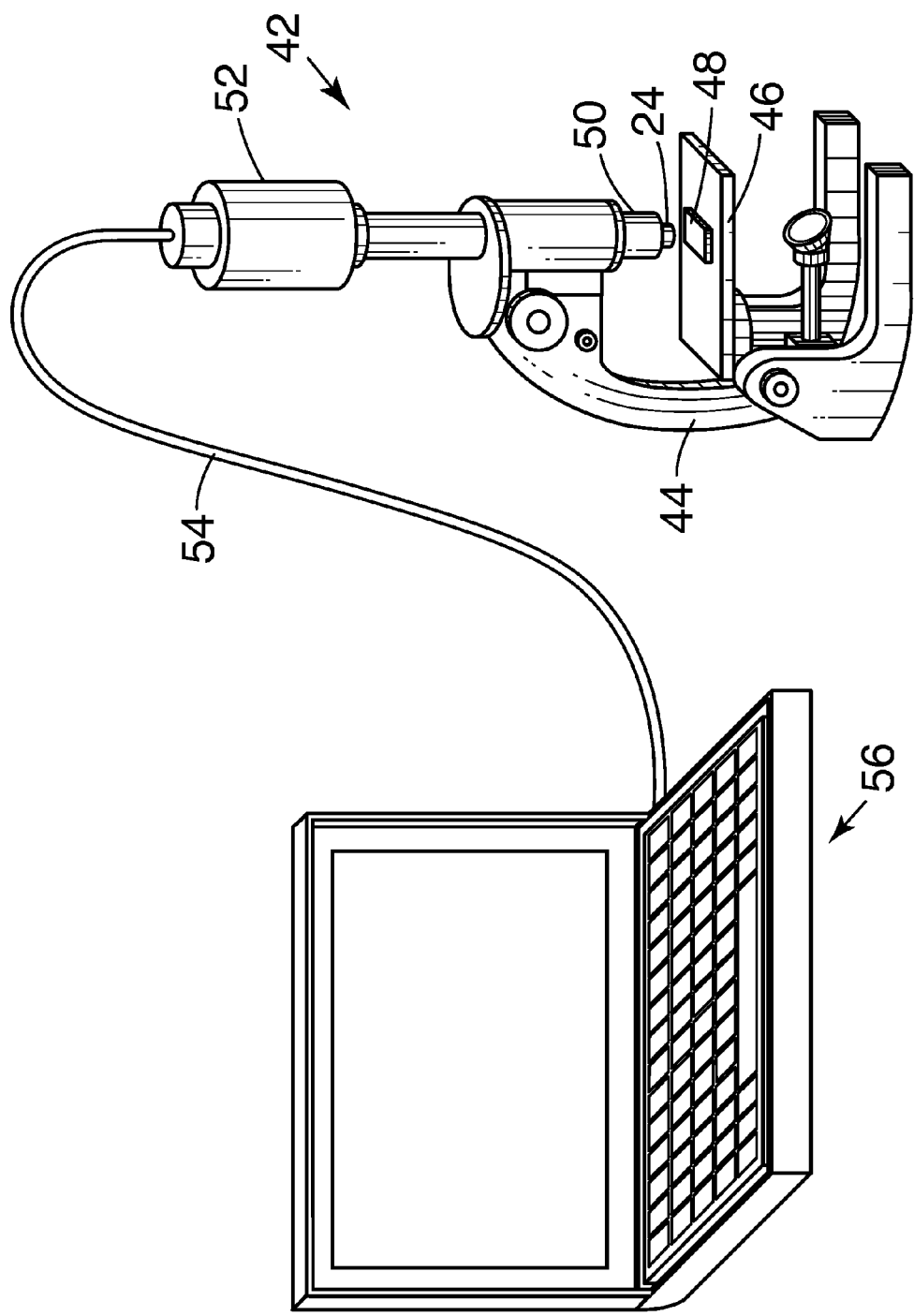
FIG. 3 is a not-to-scale schematic illustration of a near-field scanning optical microscope in accordance with an embodiment of the present invention.

One example of an instrument that utilizes the optical component of the present invention is near-field scanning optical microscope. Referring to FIG. 3, a near-field scanning optical microscope 42 can include an optical component 24 in accordance with the present invention. Briefly, a support frame 44 carries an X-axis and Y-axis traversable table 46 for supporting an analytical sample 48 to be inspected. The support frame 44 carries a Z-axis traversable nosepiece 50 for supporting a photo-detector 52 and the optical component 24, and for controlling the distance of the optical component 24 from the sample 48. The skilled artisan will recognize that traversability of the table 46 and nosepiece 50 can be interchangeable in any axis. The near-field scanning optical microscope 42 can be connected via a signal cable 54 to a data processing device such as a computer 56.

While there has been shown and described what are at present considered the preferred embodiments of the invention, it will be obvious to those skilled in the art that various changes and modifications can be prepared therein without departing from the scope of the inventions defined by the appended claims.

We claim:

1. An optical component, comprising:
   a support structure comprising a recessive phase material; and
   a plurality of noncontiguous optical conduits of at least one protrusive phase material embedded within said support structure and extending from a proximal surface to a distal surface of said optical component,
   wherein said optical conduits comprise discrete, spaced apart surface features of said protrusive phase material protruding from said support structure at said distal surface, said plurality of surface features reducing in cross sectional area away from said support structure to provide a lowest cross sectional area at a distal end of said plurality of features, wherein said protrusive phase and said recessive phase are differentially etchable by an etchant.

2. The optical component of claim 1, wherein said at least one protrusive phase material provides a higher index of refraction as compared to said recessive phase material for at least one selected wavelength or range of wavelengths of light.

3. The optical component of claim 1, wherein said index of refraction of said protrusive phase is greater than said index of refraction of said recessive phase by at least 0.01.

4. The optical component of claim 1, wherein said spaced apart surface features are arranged in an ordered array.

5. The optical component of claim 1, wherein said recessive phase comprises a first glass, and wherein said protrusive phase comprises a second glass.

6. The optical component of claim 1, further comprising a reflective material at the interface between said recessive material and said protrusive material, wherein said reflective material reflects said at least one selected wavelength or range of wavelengths of light.

7. The optical component of claim 6, wherein said reflective material comprises a metallic material.

8. The optical component of claim 1, wherein a cross section of said optical conduit at said proximal end is larger than the cross section of said conduit in contact with said support structure at said distal end.

9. The optical component of claim 1, further comprising at least one metal nanoparticle adhered to at least one of said surface features.

10. An optical instrument comprising:
    an optical component, comprising a support structure comprising a recessive phase material; and a plurality of noncontiguous optical conduits of a protrusive phase material embedded within said support structure and extending from a proximal surface to a distal surface of said optical component,
    wherein said optical conduits comprise discrete, spaced apart surface features of said protrusive phase material protruding from said support structure at said distal surface, said plurality of surface features reducing in cross sectional area away from said support structure to provide a lowest cross sectional area at a distal end of said plurality of features, wherein said protrusive phase and said recessive phase are differentially etchable by an etchant;
    a light source for illuminating a sample so that light interacts with said sample and enters said optical component through said protrusive features at said distal end of said optical component; and
    a detector in optical communication with a proximal end of said optical component for converting a light signal propagated through said optical component into an electrical signal.

11. The optical instrument of claim 10, further comprising an electrical component for supplying power to said instrument.

12. The optical instrument of claim 10, further comprising an electrical component for controlling said instrument.

13. The optical instrument of claim 10, further comprising an electrical component for processing the electrical signal into data.

14. The optical instrument of claim 13, further comprising an electrical component for displaying the data.

15. The optical instrument of claim 10, further comprising a support frame for supporting at least said optical component.

16. The optical instrument of claim 10, wherein said optical component further comprising a reflective material at the interface between said recessive material and said protrusive material, wherein said reflective material reflects said at least one selected wavelength or range of wavelengths of light.

* * * * *